United States Patent [19]

Miller et al.

[11] Patent Number: 5,001,051

[45] Date of Patent: Mar. 19, 1991

[54] DOSE CRITICAL IN-VIVO DETECTION OF ANTI-CANCER DRUG LEVELS IN BLOOD

[75] Inventors: Holly H. Miller, Bethel Island; Tomas B. Hirschfeld, deceased, late of Livermore, Calif., by Judith Hirschfeld, legal representative

[73] Assignee: Regents of the University of California, Oakland, Calif.

[21] Appl. No.: 940,972

[22] Filed: Dec. 12, 1986

[51] Int. Cl.$^5$ .................. C12Q 1/68; C07H 21/00; G01N 21/64

[52] U.S. Cl. .................. 435/6; 435/291; 435/808; 436/172; 436/905; 536/27; 935/77; 935/78; 935/86; 350/96.18; 356/38; 356/435

[58] Field of Search .................. 435/6, 291, 808; 436/172, 905; 536/27; 935/77, 78, 86; 350/96.18, 368; 356/38, 435

[56] References Cited

U.S. PATENT DOCUMENTS

| | | | |
|---|---|---|---|
| 4,419,340 | 12/1983 | Yolles | 424/19 |
| 4,488,814 | 12/1984 | Johnson | 356/414 |
| 4,559,299 | 12/1985 | Rotman | 435/29 |
| 4,577,109 | 3/1986 | Hirschfeld | 250/461.1 |
| 4,610,869 | 9/1986 | Bogden | 424/9 |
| 4,822,746 | 4/1989 | Walt | 435/528 |

OTHER PUBLICATIONS

Gaugain et al. (1978a) Biochemistry, vol. 17 (24), pp. 5071–5078.

Gaugain et al., (1986b), Biochemistry vol. 17 (24), pp. 5078–5088.

Markovits et al. (1979) Analytical Biochem. vol. 94, pp. 259–264.

Lown, J. W. (1984), in *Methods in Enzymology* (Ed. L. Packer, Academic Press, NY, NY), vol. 105, pp. 532–539.

*Primary Examiner*—Robert A. Wax
*Assistant Examiner*—Ardin H. Marschel
*Attorney, Agent, or Firm*—Shyamala T. Rajender; Nora A. Hackett; Henry P. Sartorio

[57] ABSTRACT

A method and apparatus are disclosed for the in vivo and in vitro detection and measurement of dose critical levels of DNA-binding anti-cancer drug levels in biological fluids. The apparatus comprises a laser based fiber optic sensor (optrode) which utilizes the secondary interactions between the drug and an intercalating fluorochrome bound to a probe DNA, which in turn is attached to the fiber tip at one end thereof. The other end of the optical fiber is attached to an illumination source, detector and recorder. The fluorescence intensity is measured as a function of the drug concentration and its binding constant to the probe DNA.

Anticancer drugs which lend themselves to analysis by the use of the method and the optrode of the present invention include doxorubicin, daunorubicin, carminomycin, aclacinomycin, chlorambucil, cyclophosphamide, methotrexate, 5-uracil, arabinosyl cytosine, mitomycin, cis-platinum 11 diamine dichloride procarbazine, vinblastine vincristine and the like. The present method and device are suitable for the continuous monitoring of the levels of these and other anticancer drugs in biological fluids such as blood, serum, urine and the like. The optrode of the instant invention also enables the measurement of the levels of these drugs from a remote location and from multiple samples.

12 Claims, No Drawings

DOSE CRITICAL IN-VIVO DETECTION OF ANTI-CANCER DRUG LEVELS IN BLOOD

FIELD OF THE INVENTION

The present invention relates generally to the in vivo detection and measurement of the dose critical levels of certain anti-cancer drugs in blood, serum and other biological fluids, more specifically to the detection of such drugs using a probe DNA and still more specifically to fiber optic probes for the in vivo detection and measurement of such anti-cancer drugs in biological fluids.

The United States Government has rights in this invention pursuant to DOE Contract No. W-7405-ENG-48 between the Department of Energy and the University of California for the operation of the Lawrence Livermore National Laboratory.

BACKGROUND OF THE INVENTION

Anthracyclines, and more specifically, doxorubicin, daunorubicin, carminomycin and aclacinomycin have emerged in recent years as important chemotherapeutic agents in the treatment of a broad spectrum of human cancers. Doxorubicin and daunorubicin, particularly, appear to be most useful and widely used drugs in the treatment of an unusually large number and wide variety of solid tumors and leukemias. Other drugs used in the treatment of various cancers include chlorambucil, cyclophosphamide, methotrexate, 5-uracil, arabinosyl cytosine, mitomycin, cis-platinum 11 diamine dichloride, procarbazine, vinblastine vincristine and the like. The therapeutic effect of these drugs is believed to be based on their interaction with DNA in the cell. However, chronic treatment of patients with these drugs produces irreversible heart damage and other serious complications which can be fatal if the treatment continues.

The treatment of cancer is extremely dose dependent. A 10% deficiency in the required dosage may produce no effect on the cancer while a 10% excess over the required dosage can produce serious ill effects or even death. Thus, there is a great need for measuring the therapeutic levels of these drugs in biological fluids.

U.S. Pat. No. 4,559,299 issued December 17, 1985 to Boris M. Rotman, entitled "Cytotoxicity Assays In Cell Culturing Devices", discloses a method and devices for predicting the in vivo responsiveness of cancerous cells to cytotoxic agents based on in vitro culture assessments.

U.S. Pat. No. 4,610,869 issued September 9, 1986 to Arthur E. Bogden, entitled "Method For In Vivo Testing Of Biological Response Modifiers Including Monoclonal Antibodies", describes an in vivo method for measuring the ability of biological response modifiers, including monoclonal antibodies, to interact with tumor tissue. Following the implantation of a fresh, surgical tumor in a host organism and administering to the host organism a predetermined dose of a biological response modifier, the degree of interaction between the biological response modifier and the tumor tissue is determined.

U.S. Pat. No. 4,419,340 issued December 6, 1983 to Seymour Yolles, entitled "Controlled Release Of Anti-cancer Agents From Biodegradable Polymers", describes an article and a method for controllably dispensing anti-cancer agents. The article describes biodegradable polymer shapes which contain one or more of the anti-cancer agents.

Other methods nave also been devised for the use of intercalating dyes in the detection of DNA in the cell.

In recent years, fiber optics, lasers, chemical reactions, optics and spectroscopy have been integrated to produce the new concept of remote fiber spectroscopy. This concept enables the development of small, ductile probes to detect and monitor certain chemical components in certain biological and the ambient environment. At the heart of the concept is the development of the "optrode", a fiber terminal with preselected chemical and physical properties. A single fiber is used for both excitation and for collection of the return signal, thereby keeping the sensor small and optically simple.

The general design and construction of the basic optrode is described and claimed in U.S. Pat. No. 4,577,109 issued Mar. 18, 1986 to Tomas Hirschfeld. Although, from a theoretical point of view, optrodes provide a great deal of geometric flexibility and make it possible to perform in situ, in vitro or in vivo analyses using optical spectroscopy without a line of sight, from a practical side, however, there are only a very limited number of chemical reactions which lend themselves to fiber optic spectrometry and which meet the stringent requirements for a good sensor where no preparation of the sample is possible, as is the case with in situ, in vitro or in vivo measurements. In the design of the sensor, therefore, several factors need to be taken into consideration. These factors include but are not limited to the selection of an appropriate chemical reaction which is amenable to fiber optical spectrometry, the feasibility of immobilizing or fixing the necessary reagents at one end of the optical fiber, the possible interference or disabling of the optrode by extraneous components of the sample matrix and the active shelf life of the particular optrode impregnated with the active ingredients. Therefore, selection, adaptation or development of the chemistry from the laboratory scale to the micro scale of the optrode is very complex and is thus the limiting step in the construction and development of the suitable optrode.

U.S. Pat. No. 4,488,814 issued December 18, 1984 to Leighton C. Johnson and entitled "Apparatus For And Method Of Optical Absorbance And Fluorescent Radiation Measurement", relates to an apparatus and method for optical absorbance or radiation measurement of liquid samples.

Accordingly, it is an object of the present invention to provide for the in vivo measurement of the dose critical levels of anti-cancer drugs in biological fluids.

Another object of the invention is to provide an apparatus that can be used for the in vivo or in vitro measurement and monitoring of the dose critical levels of anti-cancer drugs in biological fluids.

Yet another object is to provide a method for the continuous monitoring of the levels of anti-cancer drugs in the blood of human patients.

Another object is to monitor simultaneously multiple samples of biological fluids to measure the levels of anti-cancer drugs.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, The present invention is directed to a fiber optic probe for the in vivo detection and measurement of the concentration of nucleic acid interacting cancer treatment drugs in blood, serum and other biological fluids. The measurement is based on the inherent reaction or perturbation of the anti-cancer drugs with DNA.

The method, generally, is based on the interaction of certain indicator molecules such as fluorescent or chromophoric dyes, particularly intercalating dyes, or other suitable labels which show a dramatic increase in a detectable signal such as, for example, color change or fluorescence quantum yields when bound to DNA or RNA as compared to that of the unbound marker, label or indicator molecule. The degree of the interaction of the marker, label or indicator molecule with DNA or RNA or natural or synthetic analogs or derivatives thereof, may be measured by any suitable method such as, for example, spectrophotometric, radiometric or fluorimetric methods. Fiber optic probes are prepared by immobilizing the DNA bound marker, label or indicator molecules, preferably those with high quantum yields, at one end of an optical fiber. When the probe is exposed to an anticancer drug, such as doxorubicin or daunorubicin for example, the binding of the drug to the DNA produces a measurable change in the detectable signal such as, for example, the quantum yield of a fluorescent dye, if such is the indicator molecule used, which can then be measured as a function of the drug concentration level in the body fluid.

The device of this invention is a fiber optic sensor or probe one end of which carries a suitable support or substrate member which can or is capable of binding to and/or retaining the sensing reagents, and the other end is attached or connected to any suitable detection, recording and analyzing devices. Exemplary support or substrate members capable of binding to the sensing reagents include but are not limited to glass or ceramic beads, preferably, controlled pore glass beads, polymer beads or polymer matrix, and the like. These support matrices may optionally be pretreated or derivatized to facilitate the binding of the various reagents to them and to the fiber optic. Sensing reagents include suitable compounds which yield a detectable signal, exemplary compounds including but not limited to fluorescent and/or chromophoric dyes, particularly, intercalating dyes, radioactive markers, indicators, other biological labels and the like. The compound used as a probe, depending on the nature and type of the anticancer drug, includes DNA, RNA, natural or synthetic analogs, fragments and/or derivatives thereof.

In one embodiment of the invention, one end of a fiber optic sensor or probe assembly is attached to a controlled pore glass (cpg) bead, preferably derivatized, and which has been impregnated with a combination of a probe DNA, the fluorescent dye, and, optionally another marker or detector species. Reactive derivative groups such as diazo- or diisothiocyanate groups are attached to the surface of a controlled pore glass bead which is attached to one end of an optical fiber by means known in the art. The reactive groups facilitate the attachment or the covalent bonding of the fluorescent dye (ethidium derivative) or DNA to the surface of the glass bead. The ethidium dimer, or the DNA covalently bonded to the derivatized controlled pore glass bead then binds to the DNA or the ethidium dimer as the case may be. A change in the fluorescence of the dye, in this case, the ethidium dimer, occurs when the probe is exposed to solutions of various therapeutic drugs. The other or the second end of the fiber optic is attached to detection, recording and illumination sources as is known in the art.

Anticancer drugs which lend themselves to analysis by the use of the method and device of the present invention include doxorubicin, daunorubicin, carminomycin, aclacinomycin, chlorambucil, cyclophosphamide, methotrexate, 5-uracil, arabinosyl cytosine, mitomycin, cis-platinum 11 diamine dichloride, procarbazine, vinblastine vincristine and the like. The present method and device are suitable for the continuous monitoring of the levels of these and other anticancer drugs in biological fluids such as blood, serum, urine and the like. The optrode of the present invention lends itself to be monitored from a remote location. The optrode of the instant invention also enables the measurement of the levels of these drugs from multiple samples.

DETAILED DESCRIPTION OF THE INVENTION

The present invention is directed generally to a method and device for the in vivo or in vitro detection and measurement of the dose-critical levels of anti-cancer drugs in biological fluids, such as blood, serum, urine and the like. The method, broadly, is based on the interaction of certain label, marker or indicator molecules such as fluorescent or chromophoric dyes, particularly intercalating dyes, because of the ease of measuring the signal generated, or other suitable labels which show a dramatic increase in a detectable signal such as, for example, color change or a change in the fluorescence quantum yields when bound to the probe compound such as DNA, RNA, natural or synthetic fragments, analogs and/or derivatives thereof, as compared to that of the unbound marker, label or indicator molecule. The choice of the probe compound depends largely on the drug to be detected. The degree of the interaction of the marker, label or indicator molecule with a probe compound such as DNA, RNA, a natural or synthetic analog, fragment and/or derivative thereof, may be measured by any suitable method such as, for example, spectrophotometric, radiometric or fluorimetric methods.

As mentioned earlier, although DNA is mentioned often herein as an exemplary or preferred probe compound, such usage includes, without limitation, DNA, RNA, natural or synthetic fragments, analogs or and/or derivatives thereof, depending on the nature and structure of the anticancer drug being tested and detected. In preparing the probe assemblies of the instant invention, typically, fiber optic probe assemblies are prepared by immobilizing the DNA bound marker, label or indicator molecules, preferably those with high quantum yields, at one end of an optical fiber. Means for immobilizing the DNA or the marker separately or the DNA-bound marker at the end or the tip of a fiber optic include any suitable support medium for the purpose and includes, without limitation, glass, ceramic or polymer beads, derivatized and underivatized, polymer or other membranes normally used for the purpose. When the probe is exposed to an anticancer drug, such as doxorubicin or daunorubicin for example, the binding of the drug to the DNA produces a measurable change in the detectable signal such as, for example, the quantum yield of a fluorescent dye, if such is the indicator molecule used, which can then be measured as a function of the drug concentration level in the body fluid.

In one preferred embodiment, fiber optic probe assemblies are prepared by immobilizing DNA bound fluorescent dye molecules, preferably those with high quantum yields, at one end of an optical fiber. Means used for immobilizing the fluorescent dyes or the DNA intercalators, as these dyes are commonly referred to, include glass or ceramic beads, preferably controlled pore glass (cpg) beads, polymer beads, polymer mesh or any suitable support or matrix member which binds to or is capable of binding to the sensing reagents which are the probe compound, the marker or indicator and other secondary markers which may be optionally employed. Such DNA intercalators are usually, out not necessarily bifunctional and include compounds such as a homodimer or a heterodimer of ethidium bromide or chloride (4,7-diazadecyl-5,5'-bis(3,8-diamino-6-phenyl-phenanthridinium)dichloride dihydrochloride). When the probe is exposed to an anti-cancer drug, such as doxorubicin or daunorubicin for example, the binding of the drug to the DNA produces a change in the quantum yield of the fluorescence of the dye which can then be measured as a function of the drug concentration level in the body fluid. The other end of the fiber optic is connected to a detector, recorder and illumination sources.

In another embodiment, the device of this invention is a fiber optic sensor or probe assembly or an "optrode", to one end of which is attached a controlled pore glass (cpg) bead, preferably derivatized, and which has been impregnated with a combination of a probe DNA, the fluorescent dye, and, optionally another marker or detector species. Reactive derivative groups such as diazo- or diisothiocyanate groups are attached to the surface of a controlled pore glass bead which is attached to one end of an optical fiber by means known in the art. The reactive groups facilitate the attachment or the covalent bonding of the fluorescent dye (ethidium derivative) or DNA to the surface of the glass bead. The ethidium dimer, or the DNA covalently bonded to the derivatized controlled pore glass bead then binds to the DNA or the ethidium dimer as the case may be. A change in the fluorescence of the ethidium dimer occurs when the probe is exposed to solutions of various therapeutic drugs. The other or second end of the fiber optic is attached to detection, recording and illumination sources as is described in U.S. Pat. No. 4,577,109 referred to hereinabove.

The detection, and recording as well as the illumination sources may be included in an integral unit with the sensor or the detection and recording devices may also be located at a distant location for remote monitoring and multiple optrodes may also be attached to the same detection system, making it possible to monitor simultaneously multiple samples from a remote location as described in U.S. Pat. No. 4,577,109 and copending applications Ser. No. 909,321 filed 9/19/86 and Ser. No. 721,150 filed 4/8/85.

Various optrode configurations are possible and yield different degrees of interaction with different drugs. A DNA molecule may be bonded to the derivatized cpg and the dye then bonded to the probe DNA or the dye may be initially attached to the cpg and the DNA then bonded to the dye. One configuration includes the dye molecule sandwiched between two probe DNA molecules, one of which is bonded to the derivatized cpg. The dye may be ethidium bromide monomer, nomodimer or ethidium bromide-acridine heterodimer. An exemplary probe configuration for use with doxorubicin (adriamycin) may be schematically illustrated as:

| DITC cpg (1 ppm) | DNA (1 mg/ml) | Ethidium bromide (aq) | DNA (1 mg/ml) |

Other configurations tested include:

| DITC cpg | DNA (1 mg/ml) | acridine ethidium dimer (aq) | DNA (1 mg/ml) |

| DIAZO cpg | DNA stained iwth ethidium bromide | | |

The optrodes thus made show that ethidium bromide bonds to diazo-cpg, acridine-ethidium heterodimer bonds to DITC-cpg and ethidium homodimer bonds to DITC-cpg and respond reversibly to doxorubicin at concentrations of about 0.2 to about 10 ppm in carbonate buffer. Other anti-cancer drugs such as daunorubicin, chlorambucil, cyclophosphamide, 5-fluorouracil, bleomycin, daunorubicin, aclacinomycin, mytomycin, cis-platinum 111 diamine dichloride, procarbazine, vinblastine and vincristine sulfate, may also be tested by the use of the present optrode. The following examples are presented for purposes of illustration only and are not to be construed as limiting the invention to the illustrated examples or in any other manner or to any precise form. In the illustrated examples, the DNA used was calf thymus DNA. The diameter and pore size of the glass beads were 547 angstrom pore diameter, 20/80 mesh (as against the 122/188 mesh for the more commonly available glass beads) which made the process of attaching the beads to the fiber much easier and more rapid. The wavelengths of emission and

| ethidium bromide on diazo-cpg | Ex. 488 nm |
| | Em. 625 nm |
| ethidium homodimer on DITC-cpg | Ex. 514.5 nm |
| | Em. 639 nm |
| acridine-ethidium heterodimer on DITC-cpg | Ex. 514.5 nm |
| | Em. 615 nm |

EXAMPLE 1

Preparation Of The Probe DNA Solution

A 0.05 molar $NaHCO_3$ in HPLC purified water, adjusted to a pH of 7.4 was used for all drug preparations. Calf thymus DNA, purchased from Fluke was used in the DNA preparations. To prepare a DNA stock solution, strands of DNA were initially cut up with a clean, stainless steel scissors. 100 mg of the cut up DNA was placed in 100 ml volumetric flask and dissolved in a small amount of carbonate buffer. 7.4 mg of KCl and a grain or two of sodium azide (for antibacterial and antifungal activity) were added to the solution and the volume made up to the 100 ml mark with carbonate buffer such that the final concentration of the solution was 1 mg/ml of DNA and 10 millimolar KCl.

Both diazo and DITC derivatized control pore glass (cpg) were used to attach DNA and ethidium bromide (EB).

EXAMPLE 2

Preparation Of The Probe

Both DIAZO and DITC derivatized controlled pore glass (cpg) was used to attach DNA and the dye to the glass bead at one end of the fiber optic probe. DITC was the preferred derivative when DNA was the first component to be attached and DIAZO was the preferred derivative when the dye was the first component desired to be attached to the glass bead. Configurations successfully prepared were:

DITC-DNA-DYE-DNA
DITC-DNA-EB
DIAZO-DYE-DNA and
DITC-2ppm stained DNA.

The cpg was soaked in the DNA solution over night or at least for 8 hrs. The cpg was removed from the solution and the DNA adsorbed on the cpg was allowed to dry on the bead prior to attaching the dye. 1-2 ppm of the dye (ethidium bromide $1_{Ex\ 488nm}$) was dissolved in the carbonate buffer. The dry DNA-derivatized cpg bead was immersed in the dye solution for 4-8 hrs, followed by soaking the bead in buffer to leach out unbound dye. This was followed by soaking the bead once again in the DNA solution for 2-4 hrs. The probe was then allowed to air dry.

Prior to testing the optrode with the drug, the optrode was soaked (or conditioned) in the buffer for about 1-2 hours. The probe was then used in a buffer solution to establish a stable base line. Once a stable base line was established, the drug was added to the buffer starting with the lower concentrations and the fluorescence spectra recorded as a function of fluorescence intensity vs. emission wavelength.

Good data were obtained for probes prepared with a 1 mg/ml DNA solution made with 0.18M $Na_2CO_3$ without the addition of 10 millimolar KCl and sodium azide. All solutions of DNA without the addition of sodium azide were prepared with 0.18M sodium carbonate buffer whereas those with the addition of sodium azide were prepared with 0.18M sodium bicarbonate. The addition of 10 mM KCl aided the dissolution of DNA.

Results obtained from the previously described examples are tabulated and presented in Table 1 below:

TABLE 1

Antineoplastic Drug Sensor
Probe Configuration: DITC glass-DNA-Ethidium Bromide-DNA
Response to 2 ppm doxorubicin
Illumination: Argon Ion Laser - 1u watt
Ex: 488 nm/ Em 580-588 nm

| Conditions | Fluorescence Intensity (photon counts/sec) |
|---|---|
| Carbonate buffer pH 7.23 | I = 7.02 E4 |
| Carbonate buffer pH 7.23 (15 min) | I = 7.02 E4 |
| Carbonate buffer pH 7.23 (25 min) | I = 7.02 E4 |
| Carbonate buffer + 2 ppm Doxorubicin, pH 7.3 | I = 7.68 E4 |
| Back in carbonate buffer 7 min, pH 7.3 | I = 7.37 E4 |
| Carbonate buffer overnight, pH 7.3 | I = 5.54 E4 |
| Carbonate buffer, 2 ppm Doxorubicin, pH 7.3 (15 min) | I = 6.65 E4 |

TABLE 1-continued

Antineoplastic Drug Sensor
Probe Configuration: DITC glass-DNA-Ethidium Bromide-DNA
Response to 2 ppm doxorubicin
Illumination: Argon Ion Laser - 1u watt
Ex: 488 nm/ Em 580-588 nm

| Conditions | Fluorescence Intensity (photon counts/sec) |
|---|---|
| Carbonate buffer, 2 ppm Doxorubicin, pH 7.3 (28 min) | I = 6.66 E4 |
| Back in carbonate buffer 7 min, pH 7.3 | I = 5.92 E4 |
| Back in carbonate buffer 28 min, pH 7.3 | I = 5.67 E4 |
| Back in carbonate buffer 38 min, pH 7.3 | I = 5.50 E4 |
| Carbonate buffer, 2 ppm Doxorubicin, pH 7.3 third exposure (8 min) | I = 6.35 E4 |
| Carbonate buffer, 2 ppm Doxorubicin, pH 7.3 third exposure (15 min) | I = 6.26 E4 |
| Carbonate buffer, 2 ppm Doxorubicin, pH 7.3 third exposure (28 min) | I = 6.39 E4 |
| Back in carbonate buffer 7 min, pH 7.3 | I = 5.95 E4 |
| Back in carbonate buffer 28 min, pH 7.3 | I = 5.60 E4 |
| Back in carbonate buffer 38 min, pH 7.3 | I = 5.40 E4 |

It has thus been shown that the optrode and the method of the present invention are suitable for the measurement of the dose critical levels of anti-cancer drugs in biological fluids in vivo and in vitro. The method and device also enable the in situ measurement of the levels of such drugs but also make it possible to measure multiple samples simultaneously from a remote location.

While a particular embodiment of the invention and specific materials and parameters have been illustrated and described, the invention is not limited to the particular illustrations or embodiments so described. The above embodiments were chosen and described in order to explain best the principles and the practical application of the subject invention thereby to enable those skilled in the art to utilize the invention in various other embodiments and various modifications as are suitable for the particular use contemplated. The foregoing description of preferred embodiments of the invention have been presented therefore for purposes of illustration and description. It is not intended to be exhaustive or to limit the invention to the precise form disclosed, and obviously many modifications and variations are possible in light of the above teaching. It is intended that the scope of the invention be defined by the claims appended hereto.

What is claimed is:

1. A method for the measurement of dose-critical levels of a nucleic acid binding anti-cancer drug selected from the group consisting of chlorambucil, 5-fluorouracil, doxorubicin, daunorubicin, aclacinomycin, mitomycin, cis-platinum 11 diamine dichloride and procarbazine in a biological fluid comprising:
providing an optical fiber attached at a first end thereof to a support means;
covalently bonding a nucleic acid probe compound to the surface of said support means;
binding a sensing reagent to said nucleic acid probe compound;

connecting a second end of said optical fiber to an illuminating source and a detector means;

contacting said first end of said optical fiber with a sample fluid containing said nucleic acid binding anti-cancer drug;

detecting by said detector means the signal generated by the interaction of said probe compound with said nucleic acid binding anti-cancer drug; and measuring the intensity of the signal by calibration and comparison with known amounts of said nucleic acid anti-cancer drug and the sensing reagent.

2. The method of claim 1, wherein said nucleic acid probe compound is selected from the group consisting of DNA, RNA, natural and synthetic analogs thereof, and fragments thereof.

3. The method of claim 2, wherein said probe compound is DNA.

4. The method of claim 2, wherein said support means is selected from the group consisting of glass beads, polymer beads and polymer matrix.

5. The method of claim 4, wherein said support means is glass beads.

6. The method of claim 1, wherein said drug is doxorubicin.

7. The method of claim 1, wherein said drug is daunorubicin.

8. The method of claim 1, wherein said sensing reagent is a fluorescent dye.

9. The method of claim 8, wherein said dye is selected from the group consisting of ethidium homodimer, ethidium-acridine heterodimer, ethidium bromide, and ethidium chloride.

10. The method of claim 9, wherein said dye is ethidium homodimer.

11. The method of claim 9, wherein said dye is ethidium-acridine heterodimer.

12. A method for the measurement of dose-critical levels of a nucleic acid binding anti-cancer drug selected from the group consisting of chlorambucil, 5-fluorouracil, doxorubicin, daunorubicin, aclacinomycin, mitomycin, cis-platinum 11 diamine dichloride and procarbazine in a biological fluid comprising:

providing an optical fiber attached at a first end thereof to a controlled pore glass bead having reactive derivative groups;

covalently bonding a nucleic acid probe compound to the surface of said glass bead;

binding an intercalating fluorescent dye molecule to said nucleic acid probe compound;

connecting a second end of said optical fiber to an illuminating source and a detector means;

contacting said first end of said optical fiber with a biological fluid sample containing said nucleic acid binding anti-cancer drug;

illuminating said optical fiber to excite said dye;

detecting the fluorescence emission of said dye by said detector means; and measuring the intensity of fluorescence by calibration and comparison with known amounts of said nucleic acid binding anti-cancer drug and said dye.

* * * * *